United States Patent
Yevzlin et al.

(10) Patent No.: US 9,055,946 B2
(45) Date of Patent: Jun. 16, 2015

(54) ANASTOMOTIC CONNECTOR

(75) Inventors: Alexander Yevzlin, Madison, WI (US); Randall S. Nelson, Pine Springs, MN (US); Steven E. Scott, Excelsior, MN (US); Robert James Ziebol, Blaine, MN (US)

(73) Assignee: Phraxis Inc., Apple Valley, MN (US)

(*) Notice: Subject to any disclaimer, the term of this patent is extended or adjusted under 35 U.S.C. 154(b) by 681 days.

(21) Appl. No.: 12/626,136

(22) Filed: Nov. 25, 2009

(65) Prior Publication Data

US 2010/0130995 A1 May 27, 2010

Related U.S. Application Data

(60) Provisional application No. 61/118,267, filed on Nov. 26, 2008.

(51) Int. Cl.
*A61B 17/11* (2006.01)
(52) U.S. Cl.
CPC .......... *A61B 17/11* (2013.01); *A61B 2017/1107* (2013.01); *A61B 2017/1135* (2013.01)
(58) Field of Classification Search
CPC ............... A61B 2017/1135; A61B 2017/1107; A61B 17/11
USPC .................................................. 606/151–156
See application file for complete search history.

(56) References Cited

U.S. PATENT DOCUMENTS

| | | | |
|---|---|---|---|
| 3,818,511 A * | 6/1974 | Goldberg et al. | 623/1.31 |
| 4,512,761 A | 4/1985 | Raible | |
| 5,456,712 A | 10/1995 | Maginot | |
| 5,755,775 A | 5/1998 | Trerotola | |
| 5,755,778 A | 5/1998 | Kleshinski | |
| 5,968,089 A * | 10/1999 | Krajicek | 623/1.15 |

(Continued)

FOREIGN PATENT DOCUMENTS

| | | |
|---|---|---|
| CA | 2366703 A1 | 9/2000 |
| CA | 2574941 A1 | 7/2007 |

(Continued)

OTHER PUBLICATIONS

Japanese Office Action issued by the Japanese Patent Office (translated), regarding corresponding patent application Serial No. 2014-516024, mailed Oct. 15, 2014; 5 pages.

(Continued)

*Primary Examiner* — Julian W Woo
*Assistant Examiner* — Shaun L David
(74) *Attorney, Agent, or Firm* — Barbara A. Wrigley; Oppenheimer Wolff & Donnelly LLP

(57) ABSTRACT

An anastomotic connector comprises a generally tubular access port having a first end and a second end and a main body portion in fluid communication with the second end of the access port that is structured to be deployed within a fluid passageway. The main body portion includes an expandable mesh frame defining a pair of flanges extending outwardly from the second end of the access port and a retention strap extending across the second end of the access port. The pair of flanges and the retention strap are structured to exert a radial force on an internal surface of a fluid passageway when the mesh frame of the main body portion is expanded within the fluid passageway. Furthermore, the pair of flanges and the retention strap allow the passage of fluid to the distal tissues that the native fluid passageway is supplying.

9 Claims, 12 Drawing Sheets

(56) References Cited

U.S. PATENT DOCUMENTS

| | | | |
|---|---|---|---|
| 5,972,017 A * | 10/1999 | Berg et al. | 606/198 |
| 6,030,395 A * | 2/2000 | Nash et al. | 606/153 |
| 6,179,848 B1 | 1/2001 | Solem | |
| 6,210,429 B1 * | 4/2001 | Vardi et al. | 623/1.11 |
| 6,241,743 B1 * | 6/2001 | Levin et al. | 606/153 |
| 6,402,767 B1 * | 6/2002 | Nash et al. | 606/153 |
| 6,451,048 B1 | 9/2002 | Berg et al. | |
| 6,458,140 B2 * | 10/2002 | Akin et al. | 606/153 |
| 6,464,665 B1 | 10/2002 | Heuser | |
| 6,464,709 B1 * | 10/2002 | Shennib et al. | 606/155 |
| 6,482,214 B1 * | 11/2002 | Sidor et al. | 606/151 |
| 6,485,513 B1 * | 11/2002 | Fan | 623/1.36 |
| 6,517,558 B2 * | 2/2003 | Gittings et al. | 606/153 |
| 6,582,463 B1 | 6/2003 | Mowry et al. | |
| 6,585,760 B1 | 7/2003 | Fogarty | |
| 6,599,303 B1 * | 7/2003 | Peterson et al. | 606/153 |
| 6,682,540 B1 | 1/2004 | Sancoff et al. | |
| 6,719,781 B1 | 4/2004 | Kim | |
| 6,743,243 B1 * | 6/2004 | Roy et al. | 606/153 |
| 6,855,162 B2 | 2/2005 | Parodi | |
| 7,025,773 B2 * | 4/2006 | Gittings et al. | 606/153 |
| 7,056,326 B2 | 6/2006 | Bolduc et al. | |
| 7,105,020 B2 * | 9/2006 | Greenberg et al. | 623/1.35 |
| 7,175,652 B2 | 2/2007 | Cook et al. | |
| 7,591,827 B2 * | 9/2009 | Hill et al. | 606/153 |
| 7,611,523 B2 | 11/2009 | Vargas et al. | |
| 7,691,140 B2 | 4/2010 | Bates et al. | |
| 7,722,665 B2 | 5/2010 | Anwar et al. | |
| 7,766,955 B2 * | 8/2010 | Vardi et al. | 623/1.15 |
| 7,828,834 B2 | 11/2010 | Garbe | |
| 7,850,725 B2 * | 12/2010 | Vardi et al. | 623/1.15 |
| 7,892,247 B2 * | 2/2011 | Conston et al. | 606/155 |
| 7,927,343 B2 * | 4/2011 | Hill et al. | 606/153 |
| 8,287,586 B2 | 10/2012 | Schaeffer et al. | |
| 8,298,251 B2 | 10/2012 | Golden et al. | |
| 8,343,204 B2 | 1/2013 | Osborne | |
| 8,361,092 B1 | 1/2013 | Asfora | |
| 8,366,651 B2 | 2/2013 | Dakin et al. | |
| 8,439,963 B2 | 5/2013 | Dickinson et al. | |
| 8,486,153 B2 | 7/2013 | Levine et al. | |
| 8,551,127 B2 | 10/2013 | Asfora et al. | |
| 8,628,583 B2 | 1/2014 | Meade et al. | |
| 8,715,336 B2 | 5/2014 | Chu et al. | |
| 8,728,145 B2 | 5/2014 | Chuter et al. | |
| 2002/0022853 A1 | 2/2002 | Swanson et al. | |
| 2002/0099392 A1 | 7/2002 | Mowry et al. | |
| 2002/0123790 A1 | 9/2002 | White et al. | |
| 2003/0144578 A1 | 7/2003 | Koster, Jr. | |
| 2004/0102794 A1 * | 5/2004 | Roy et al. | 606/153 |
| 2004/0107004 A1 | 6/2004 | Levine et al. | |
| 2005/0171598 A1 | 8/2005 | Schaeffer | |
| 2005/0192604 A1 * | 9/2005 | Carson et al. | 606/153 |
| 2005/0228409 A1 | 10/2005 | Coppi | |
| 2005/0267559 A1 | 12/2005 | De Oliveira | |
| 2007/0106313 A1 | 5/2007 | Golden et al. | |
| 2007/0185567 A1 | 8/2007 | Heuser et al. | |
| 2007/0203572 A1 | 8/2007 | Heuser et al. | |
| 2008/0288044 A1 | 11/2008 | Osborne | |
| 2009/0036817 A1 | 2/2009 | Dakin et al. | |
| 2009/0076587 A1 | 3/2009 | Cully et al. | |
| 2009/0143793 A1 | 6/2009 | Chua et al. | |
| 2010/0010613 A1 | 1/2010 | Dorn | |
| 2011/0118821 A1 | 5/2011 | Brocker et al. | |
| 2011/0172684 A1 | 7/2011 | Granja Filho | |
| 2011/0282368 A1 | 11/2011 | Swayze et al. | |
| 2012/0065652 A1 | 3/2012 | Cully et al. | |
| 2012/0123513 A1 | 5/2012 | Asfora et al. | |
| 2012/0290065 A1 | 11/2012 | Li et al. | |
| 2013/0035752 A1 | 2/2013 | Chang | |
| 2013/0274646 A1 | 10/2013 | Paris et al. | |
| 2014/0031785 A1 | 1/2014 | Schwagten et al. | |
| 2014/0121585 A1 | 5/2014 | Baker et al. | |

FOREIGN PATENT DOCUMENTS

| | | |
|---|---|---|
| CA | 2766347 A1 | 12/2010 |
| CA | 2810671 | 3/2012 |
| WO | WO-98-19629 A2 | 5/1998 |
| WO | WO-98-19636 A2 | 5/1998 |
| WO | WO 99/45861 | 9/1999 |
| WO | WO 01/12074 A1 | 2/2001 |
| WO | WO 01/49213 A2 | 7/2001 |
| WO | WO 01/49213 A3 | 7/2001 |
| WO | WO-2004-010898 A1 | 2/2004 |
| WO | WO-2004-093966 A1 | 11/2004 |
| WO | WO-2009-055651 A1 | 4/2009 |
| WO | WO 2010/121192 A1 | 10/2010 |
| WO | WO 2012/117402 A1 | 9/2012 |

OTHER PUBLICATIONS

Japanese Office Action issued by the Japanese Patent Office (translated), regarding corresponding patent application Serial No. 2014-514937, mailed Oct. 15, 2014; 6 pages.

Japanese Office Action issued by the Japanese Patent Office (translated), regarding corresponding patent application Serial No. 2014-516037, mailed Oct. 15, 2014; 5 pages.

* cited by examiner

ANASTOMOTIC CONNECTOR

CROSS-REFERENCE TO RELATED APPLICATION(S)

This application claims the benefit of U.S. Provisional Application Ser. No. 61/118,267, filed Nov. 26, 2008, the entirety of which is hereby incorporated by reference.

BACKGROUND OF THE INVENTION

This invention relates to anastomotic connector devices. In particular, this invention relates to a vascular access device for use in hemodialysis and other procedures, such as in the cardiovascular field, where short-term and long-term access is required.

In the United States alone, approximately 400,000 people have end-stage renal disease requiring chronic hemodialysis. Hemodialysis replaces kidney function by removing toxins from the blood that are normally removed by healthy kidneys. In order to effectively remove toxins, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula.

Typically, a vein may be directly attached to an artery, but it takes from six to eight weeks before the fistula has sufficiently matured (time between placement and cannulation for dialysis) to provide adequate blood flow for use with hemodialysis. Moreover, a direct anastomosis may not be feasible in all patients due to anatomical considerations. Other patients may require the use of artificial graft material to provide an access site between the arterial and venous vascular systems. Because of the length of time required for a fistula to mature a patient needing dialysis will typically require a temporary access device, such as a Quinton catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional rise in catheter use has been documented. What is needed is an improved vascular access device that addresses the foregoing problems.

BRIEF SUMMARY OF THE INVENTION

The present invention solves the foregoing problems by allowing a percutaneous connection to be created between an artery and vein in the arm of a kidney failure patient without the need for surgery; which allows immediate cannulation of the connection without reliance on catheter use; and which allows for the maturation of the outflow veins for subsequent conversion to a fistula.

In one aspect of the present invention, an anastomotic connector is provided that comprises a generally tubular access port having a first end and a second end and a main body portion in fluid communication with the second end of the access port that is structured to be deployed within a fluid passageway. The main body portion includes an expandable mesh frame defining a pair of flanges extending outwardly from the second end of the access port and a retention strap extending across the second end of the access port. An alternate embodiment of the invention may include a collapsible, yet resilient structure in lieu of the mesh. The pair of flanges and the retention strap are structured to exert a radial force on an internal surface of a fluid passageway when the mesh frame of the main body portion is expanded within the fluid passageway. The width of the retention strap may be less than that of the flanges to facilitate insertion into the fluid passageway. The pair of flanges and the retention strap allow the passage of fluid (blood, etc.) to the distal tissues that the native vessel is supplying.

In another aspect of the present invention, a method of positioning an anastomotic connector within a fluid passageway comprises the steps of: (i) providing an anastomotic connector including a generally tubular access port having a first end and a second end and a main body portion in fluid communication with the second end of the access port, wherein the main body portion includes an expandable mesh frame defining a pair of flanges extending outwardly from the second end of the access port and a retention strap extending across the second end of the access port; (ii) loading the anastomotic connector into a deployment sheath; (iii) introducing a distal end of the deployment sheath through an access site in a fluid passageway; and (iv) deploying the main body portion through the distal end of the deployment sheath and into the fluid passageway, wherein upon deployment the pair of flanges and the retention strap are expanded to exert a radial force on an internal surface of the fluid passageway.

DETAILED DESCRIPTION OF THE INVENTION

Generally speaking, the present invention is directed to an anastomotic connector structured to attach a dialysis graft between an artery and a vein. The anastomotic connectors in accordance with the present invention may be placed percutaneously or subcutaneously in either an artery or a vein, and may be fabricated from any biocompatible material suitable for implantation into the human body. Further, the anastomotic connectors preferably have a low cost and are readily replaceable. As will be appreciated by those skilled in the art based upon the following disclosure, the anastomotic connectors of the present invention may replace the use of catheters in those patients on hemodialysis who are permanently consigned to catheter use due to their inability (anatomically or otherwise) to sustain long-term fistula or graft options.

Numerous structural variations of an anastomotic connector device are contemplated and within the intended scope of the present invention. For purposes of discussion and not limitation, several exemplary embodiments will be described in detail below. As those skilled in the art will appreciate, the teachings with regard to one exemplary embodiment may apply to the other exemplary embodiments even if not specifically stated. Thus, the scope of the present invention may be derived by the combined teachings set forth herein. Furthermore, although the anastomotic connectors will be described with reference to placement within an artery, it should be understood that the anastomotic connectors may be placed within various other fluid passageways including, but not limited to, a vein or the like.

Figure 1:
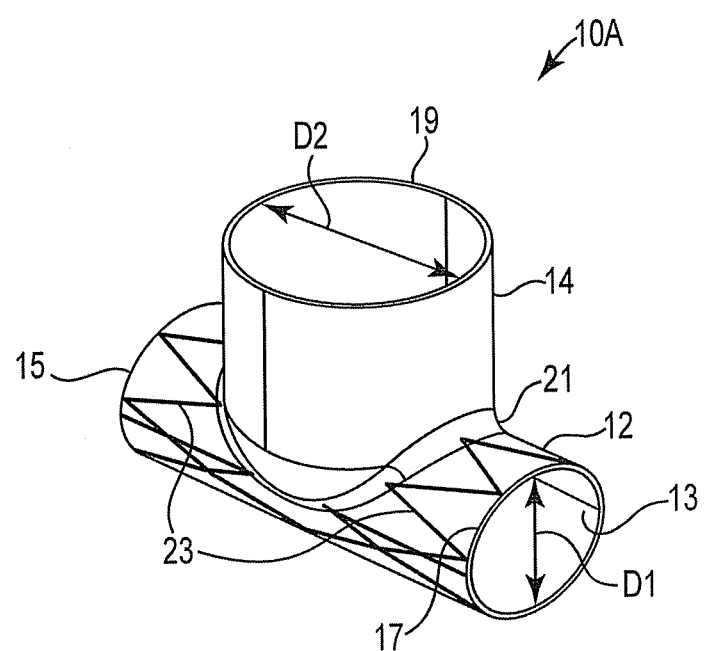
FIG. 1 is a perspective view of a first exemplary embodiment of an anastomotic connector in accordance with the present invention.

FIG. 1 is a perspective view of an anastomotic connector 10A, which is a first exemplary embodiment of an anastomotic connector in accordance with the present invention. As illustrated in FIG. 1, anastomotic connector 10A generally includes a main body 12 with a side access port 14 extending outwardly therefrom. Main body 12 includes an open first end 15 and an open second end 17. Side access port 14 extends substantially perpendicular from main body 12 about midway between first end 15 and second end 17. For this reason, anastomotic connector 10A may be referred to as a. "T" connector due to its "T" shaped structure. Side access port 14 includes an open first end 19 and a second end 21 that is in fluid communication with an interior of main body 12.

Although anastomotic connector 10A is illustrated and described as a "T" connector, those skilled in the art will appreciate that other configurations are also contemplated and within the intended scope of the present invention. For example, in one alternative embodiment side access port 14 may extend from main body 12 at a location adjacent to either first end 15 or second end 17, thereby more closely resembling an "L" than a "T." In another alternative embodiment, side access port 14 may extend from main body 12 in a non-perpendicular direction. Other configurations of side access port 14 are also possible as will be appreciated by those skilled in the art.

Main body 12 is a generally tubular structure having a diameter D1, while side access port 14 is a generally tubular structure having a diameter D2. As illustrated in FIG. 1, diameter D2 is greater than diameter D1. However, in other embodiments diameter D2 may be less than diameter D1, or alternatively, diameters D1 and D2 may be substantially equivalent. The diameters of main body 12 and side access port 14 may depend upon numerous factors including, but not limited to, the implant location of main body 12 or the desired amount of flow into or out of side access port 14. As will be appreciated by those skilled in the art, diameter D2 may be sized similar to or slightly larger than the diameter of the arterial opening through which the anastomotic connector will be deployed. As will further be appreciated by those skilled in the art, diameter D1 may be sized similar to or slightly lager than the internal diameter of the artery into which the connector will be deployed. In one exemplary embodiment diameter D1 may be in a range between about 1 mm and about 4 mm and diameter D2 may be in a range between about 2 mm and about 10 mm.

As illustrated in the exemplary embodiment of FIG. 1, main body 12 of anastomotic connector 10A includes mesh frame 23. As will be appreciated by those skilled in the art, mesh frame 23 may be structured to provide rigidity and reinforcement to main body 12 when anastomotic connector 10A is deployed within an artery. Mesh frame 23 may be either self-expanding or non self-expanding. One benefit of using a self-expanding material is that main body 12 will expand when deployed within an artery without the need for a separate expansion device, thus eliminating additional equipment and steps during the deployment process. On the other hand, one benefit of using a non self-expanding material is that a surgeon maintains control over the instant in time when main body 12 is expanded and the "amount" of expansion.

Exemplary "self-expanding" materials that may be used to create the mesh frame include, but are not limited to, shape memory alloys such as nitinol, stainless steel, or various polymers. Nitinol may be preferable due to its high yield strain. However, any suitable self-expanding mesh frame material may be used as will be appreciated by those skilled in the art. Furthermore, although any suitable non self-expanding mesh frame material may be used, exemplary materials may include stainless steel, titanium, or the like.

Main body 12 and side access port 14 of anastomotic connector 10A may be formed using any suitable biocompatible material as will be appreciated by those skilled in the art. Such biocompatible materials may include, but are not limited to, expanded Polytetrafluoroethylene ("ePTFE"), polyester, porcine vessel, THORALON® (a self-sealing polyurethane material), Polytetrafluoroethylene ("PTFE") modified with urea (such as the VECTRA® graft), silicone composites, or various other plastics and elastomers or combinations thereof. Thus, in one exemplary embodiment main body 12 of anastomotic connector 10A may be structured as an ePTFE covered mesh frame. Side access port 14 may also be formed from ePTFE, or alternatively from any one of the other suitable biocompatible materials. Thus, the various components of anastomotic connector 10A may be formed using the same or different materials without departing from the intended scope of the present invention.

As illustrated in FIG. 1, the biocompatible covering 13 of main body 12 is formed on an inner surface of mesh frame 23. In other embodiments, biocompatible covering 13 may be formed on an outer surface of the mesh frame, or alternatively on both the inner and outer surfaces of the mesh frame without departing from the intended scope of the present invention.

Regardless of the exact construction, it may be preferable to provide the anastomotic connectors of the present invention with an inner surface that is contoured to allow smooth arterial or venous blood flow into and out of the connector device. As those skilled in the art will appreciate, providing a non-thrombogenic surface minimizes the creation of recirculation or stagnation zones with high shear or dwell times that could otherwise lead to clotting.

Although anastomotic connector 10A is illustrated as having only main body 12 reinforced with a mesh frame, those skilled in the art will appreciate that other configurations are also possible. In one alternative embodiment only side access port 14 is reinforced with a mesh frame. In another alternative embodiment both main body 12 and side access port 14 are reinforced with a mesh frame. Additionally, the mesh reinforcement may be used across all or only part of main body 12 and/or side access port 14. For example, mesh frame 23 of FIG. 1 may be modified such that it does not extend the entire length of main body 12 between first end 15 and second end 17.

In addition to using various combinations of mesh-reinforced and non mesh-reinforced components, the type of mesh frame material (i.e., self-expanding or non self-expanding) may also be varied. For example, in one embodiment side access port 14 may be formed from a non self-expanding mesh frame material, while main body 12 may be formed from a self-expanding mesh frame material. In another embodiment, side access port 14 may be formed from a self-expanding mesh frame material, while main body 12 may be formed from a non self-expanding mesh frame material. In another embodiment, both side access port 14 and main body 12 may be formed from a self-expanding mesh frame material. In yet another embodiment, both side access port 14 and main body 12 may be formed from a non self-expanding mesh frame material.

As will be discussed in further detail to follow, a first one of the anastomotic connectors 10A may be implanted through the sidewall of an artery in such a way that main body 12 is substantially concentric and in contact with the internal arterial wall, while side access port 14 protrudes through the sidewall at the site of implant. A second one of the anastomotic connectors 10A may be implanted through the sidewall of a vein in such a way that main body 12 is substantially concentric and in contact with the internal venous wall, while side access port 14 protrudes through the sidewall at the site of implant. A dialysis graft or the like may be attached to the first and second anastomotic connectors to provide a fluid pathway between the vein and the artery.

Figure 2:
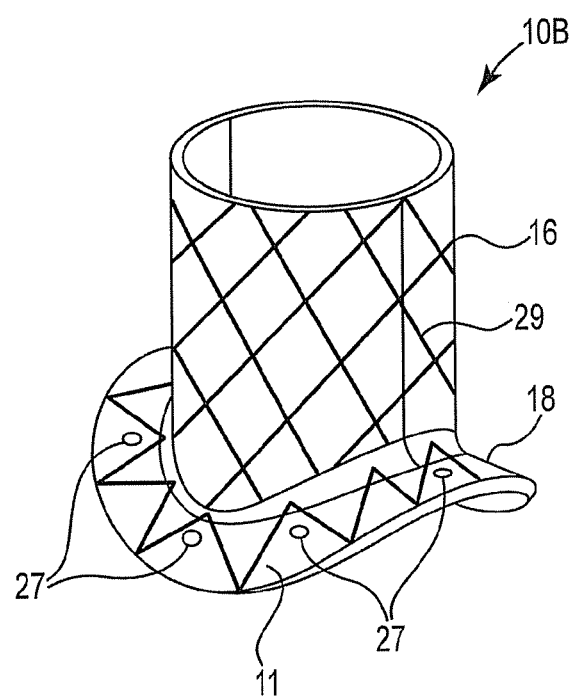
FIG. 2 is a perspective view of a second exemplary embodiment of an anastomotic connector in accordance with the present invention.

FIG. 2 is a perspective view of an anastomotic connector 10B, which is a second exemplary embodiment of an anastomotic connector in accordance with the present invention. Anastomotic connector 10B may be referred to as a "tophat" connector due to its hat-like structure formed by a side access port 16 having a flanged distal end 18. Thus, anastomotic connector 10B is generally similar to anastomotic connector 10A described above with reference to FIG. 1, but substitutes main body 12 with flanged distal end 18. As will be appreciated by those skilled in the art, flanged distal end 18 includes an outer surface 11 that is structured and contoured to engage an internal surface of an artery adjacent to the location where side access port 16 exits the artery.

As further illustrated in FIG. 2, anastomotic connector 10B may optionally include mesh frame 29 that is structured to provide rigidity and reinforcement to side access port 16 and flanged distal end 18 when anastomotic connector 10B is deployed within an artery. Similar to the mesh frames discussed above with reference to anastomotic connector 10A of FIG. 1, mesh frame 29 may be either self-expanding or non self-expanding. For example, anastomotic connector 10B may be structured as an ePTFE covered self-expanding mesh frame formed from nitinol, or a non self-expanding mesh frame formed from stainless steel or titanium. However, as discussed above with reference to anastomotic connector 10A, any suitable mesh frame material and cover material may be used without departing from the intended scope of the present invention.

In one exemplary embodiment of anastomotic connector 10B, flanged distal end 18 may include a plurality of hooks or engagement members (not shown) structured to engage the internal arterial wall after implantation. When present, the hooks may be structured to extend through a plurality of apertures 27 spaced around flanged distal end 18. However, hooks or engagement members are not a necessary component of the present invention and anastomotic connector 10B may be securely implanted within an artery without the need for such "attachment" means.

As will be appreciated by those skilled in the art, anastomotic connector 10B may be implanted through the sidewall of an artery and positioned such that flanged distal end 18 expands into shape and substantially conforms to the adjacent internal arterial wall. In the embodiment of the anastomotic connector 10B that includes a plurality of hooks on the flanged distal end 18, the hooks may be structured to engage with the internal arterial wall as a means for anchoring the connector as the connector is being pulled against the internal arterial wall. In another exemplary embodiment, anastomotic connector 10B may optionally include an external locking ring (not shown) structured to secure the arterial wall against the connector flange so that the arterial wall does not necrose due to excessive pressure against the wall.

Figure 3:
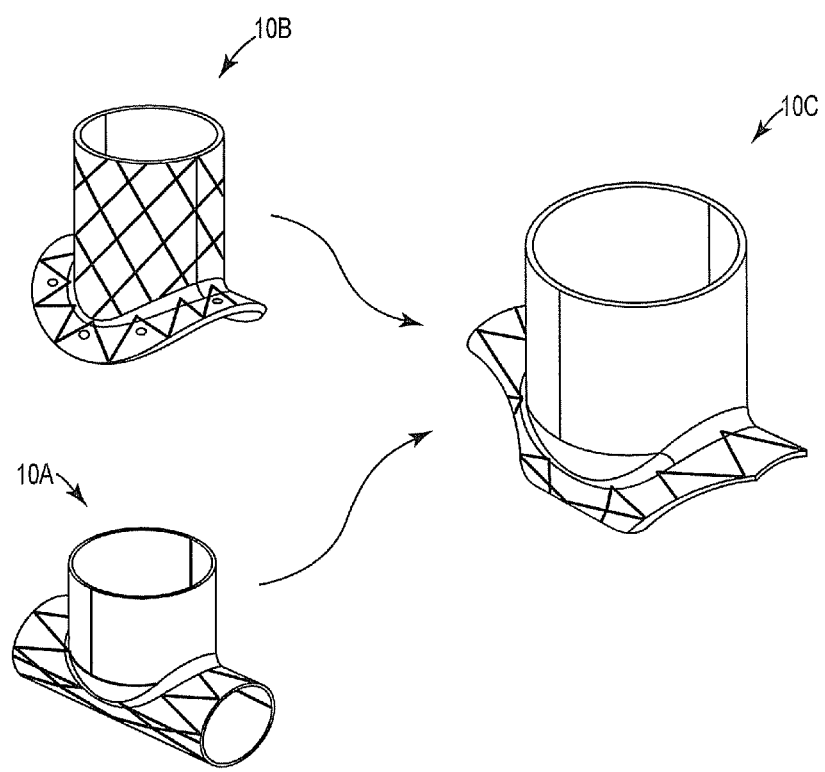
FIG. 3 is a diagram illustrating a third exemplary embodiment of an anastomotic connector in accordance with the present invention, which is a combination of the first and second exemplary embodiments illustrated in FIGS. 1 and 2.

FIG. 3 is a diagram illustrating an anastomotic connector 10C, which is a third exemplary embodiment of an anastomotic connector in accordance with the present invention. As will be apparent to those skilled in the art, anastomotic connector 10C may generally be viewed as a combination or hybridization of the anastomotic connector 10A of FIG. 1 and the anastomotic connector 10B of FIG. 2.

Figure 4:
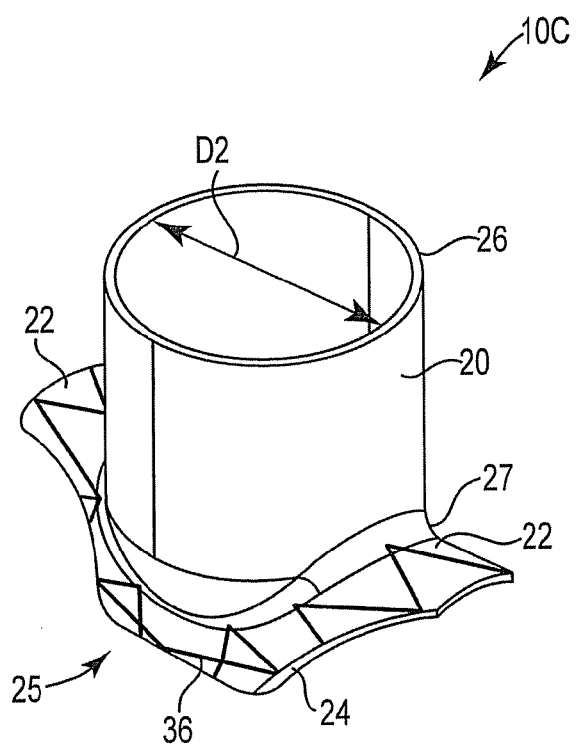
FIG. 4 is a perspective view of the anastomotic connector of FIG. 3.
Figure 5A:
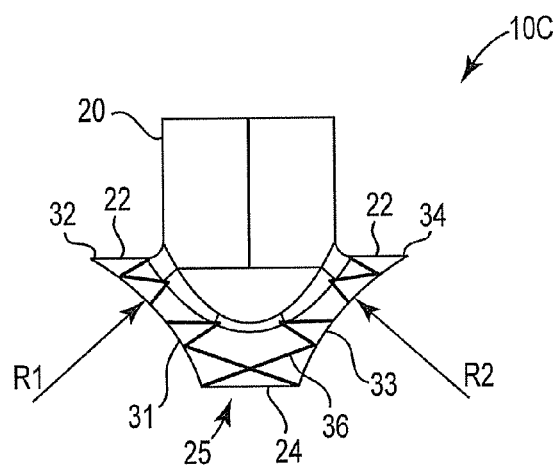
FIGS. 5A-5C are front, end, and top views of the anastomotic connector of FIG. 3.
Figure 5B:
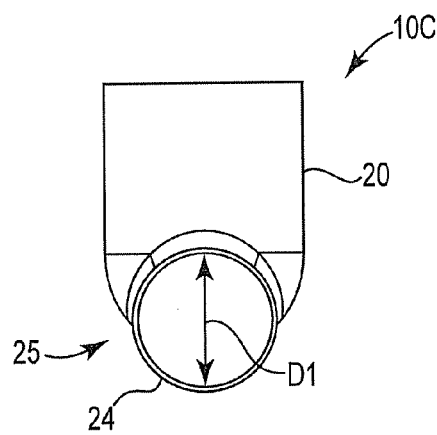
Figure 5C:
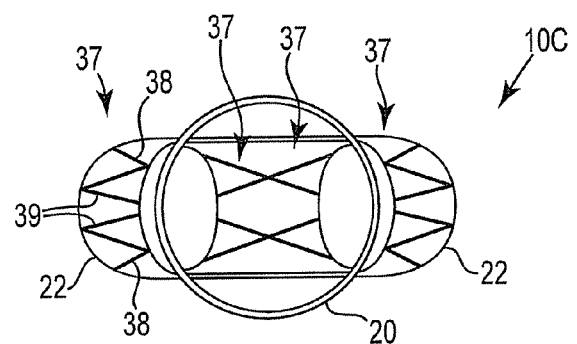

FIG. 4 is a perspective view of the anastomotic connector 10C illustrated in FIG. 3. Additionally, FIGS. 5A, 5B, and 5C are front, end, and top views, respectively, of the anastomotic connector 10C. Generally speaking, and as shown in FIGS. 4 and 5A-5C, anastomotic connector 10C is structured as a "tophat" with a "retention strap." More particularly, anastomotic connector 10C may include a main body or bonnet 25 with a side access port 20 extending outwardly therefrom. Side access port 20 extends substantially perpendicular from bonnet 25 and includes an open first end 26 and a second end 27 that is in fluid communication with an interior of bonnet 25. Bonnet 25 includes an upper portion adjacent to second end 27 of side access port 20 having a pair of flanges 22 and a lower portion having a retention strap 24 extending across the second end 27 of the side access port 20.

Side access port 20 is a generally tubular structure having a diameter D2 similar to that described above with reference to anastomotic connector 10A. Bonnet 25 forms a partial tubular structure with a diameter D1 that is also similar to that described above with reference to anastomotic connector 10A. Thus, diameter D1 is preferably similar to or slightly lager than the internal diameter of the artery into which the connector will be deployed. Once again, although diameter D1 is illustrated as being less than diameter D2, in other embodiments diameter D2 may be less than diameter D1, or alternatively, diameters D1 and D2 may be substantially equivalent.

As best illustrated in FIGS. 4 and 5A, bonnet 25 may be structured as a tubular member having a "cutout" portion on each end of the member. Particularly, these "cutouts" may create a first contoured edge 31 adjacent to a first end 32 of the bonnet 25 and a second contoured edge 33 adjacent to a second end 34 of the bonnet 25. The first and second contoured edges 31 and 33 are structured to define the pair of flanges 22 at the upper portion of the bonnet 25 and the retention strap 24 at the lower portion of the bonnet 25. As illustrated in FIG. 5A, the first contoured edge 31 may be defined by a substantially constant first radius of curvature R1 and the second contoured edge 33 may be defined by a substantially constant second radius of curvature R2. The values of the first and second radii of curvature R1 and R2 may be substantially equivalent as illustrated in FIG. 5A, although the curvature values may also be different as will be appreciated by those skilled in the art.

Although first and second contoured edges 31 and 33 are described and illustrated as having a substantially constant curve or radius, anastomotic connector embodiments having first and second contoured edges with a curve or radius that is variable are also contemplated and within the intended scope of the present invention. Additionally, embodiments having first and second edges that are defined by substantially straight edges are also contemplated.

As illustrated in FIGS. 4 and 5A-5C, bonnet 25 of anastomotic connector 10C includes mesh frame 36. As will be appreciated by those skilled in the art, mesh frame 36 may be structured to provide rigidity and reinforcement to bonnet 25 when anastomotic connector 10C is deployed within an artery. As discussed above with regard to the mesh frames of anastomotic connectors 10A and 10B, mesh frame 36 may be either self-expanding or non self-expanding, and may be formed using any suitable material. For example, bonnet 25 of anastomotic connector 10C may be structured as an ePTFE covered self-expanding mesh frame formed from nitinol, or a non self-expanding mesh frame formed from stainless steel or titanium. However, as discussed above with reference to the anastomotic connector 10A, any suitable mesh frame material and cover material may be used without departing from the intended scope of the present invention. Side access port 20, which does not include a mesh frame for reinforcement in the illustrated embodiment, may be formed from any suitable biocompatible material as previously discussed. The material may be the same as that used to "cover" mesh frame 36, such as ePTFE in the above example. However, use of the same biocompatible material for both bonnet 25 and side access port 20 is not necessary.

Mesh frame 36 of bonnet 25 may be structured in any suitable configuration that allows for expansion and contraction of the frame. In one exemplary embodiment as illustrated best in FIG. 5C, mesh frame 36 may be structured as a series of mesh rows 37 in a "zigzag" or "sinusoidal" configuration, wherein each of the mesh rows is defined by alternating peaks 38 and troughs 39. In order to connect the mesh rows together and create the frame structure, a peak 38 in one mesh row 37 may be joined to a corresponding trough 39 in an adjacent one of the mesh rows. However, it is not necessary to join each peak 38 to a corresponding trough 39 as will be appreciated by those skilled in the art.

Figure 6A:
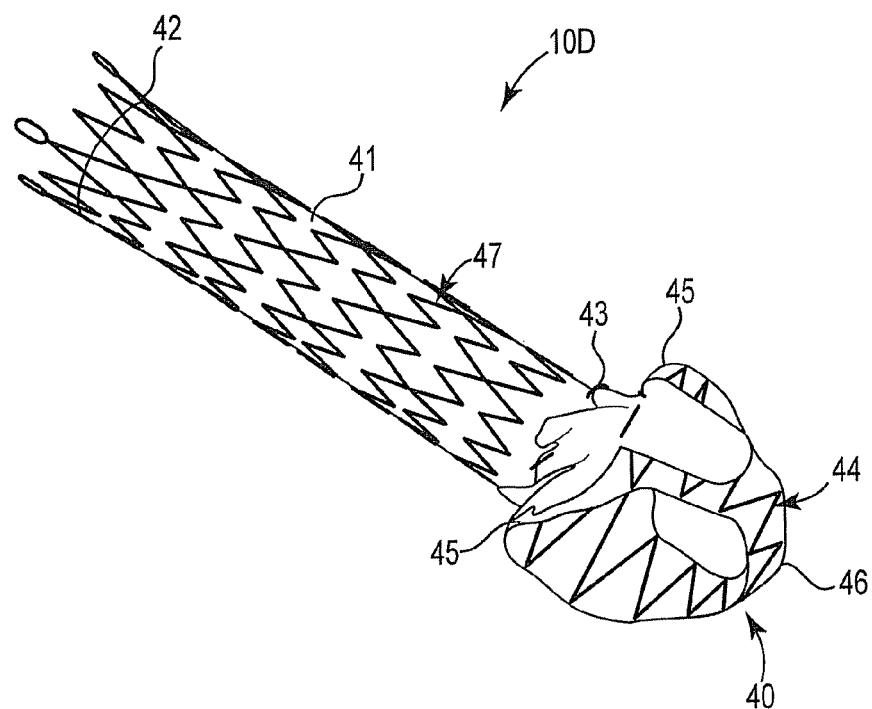
FIGS. 6A-6B are perspective and front views, respectively, of a fourth exemplary embodiment of an anastomotic connector in accordance with the present invention.
Figure 6B:
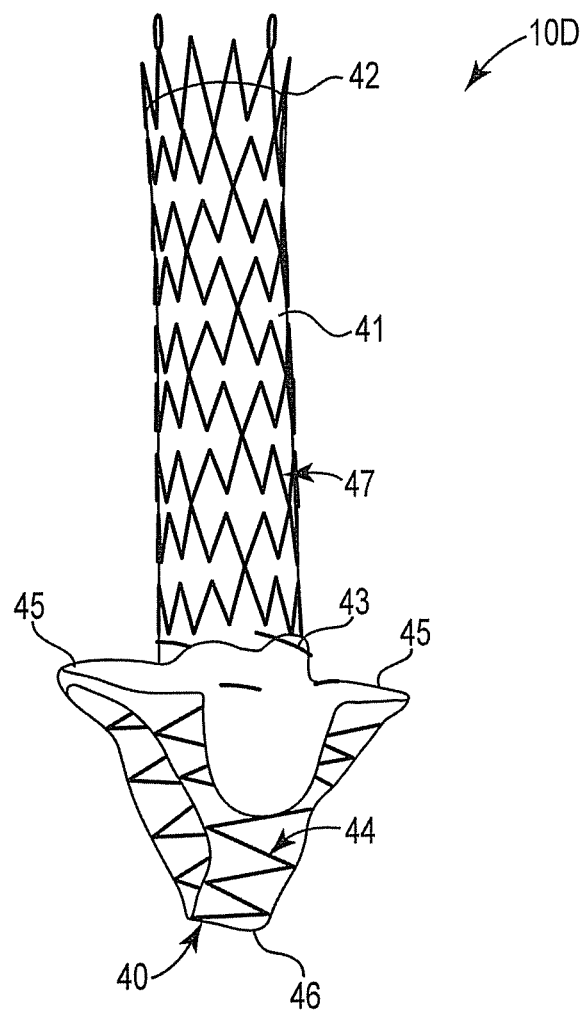

FIGS. 6A and 6B are diagrams illustrating perspective and front views, respectively, of another exemplary anastomotic connector 10D in accordance with the present invention. Anastomotic connector 10D is similar to anastomotic connector 10C previously described above with reference to FIGS. 3, 4, and 5A-5C, and generally includes a main body or bonnet 40 with a side access port 41 extending outwardly therefrom. Once again, side access port 41 extends substantially perpendicular from bonnet 40 and includes an open first end 42 and a second end 43 that is in fluid communication with an interior of bonnet 40. Bonnet 40, which is reinforced by a mesh frame 44, includes an upper portion adjacent to second end 43 of side access port 41 having a pair of flanges 45 and a lower portion having a retention strap 46 extending across the second end 43 of the side access port. However, unlike anastomotic connector 10C, the side access port 41 of anastomotic connector 10D is also reinforced by a mesh frame 47. As will be appreciated by those skilled in the art, mesh frame 47 may be structured to provide rigidity and reinforcement to side access port 41 and prevent the port from becoming kinked so as to maintain an open fluid path through the port when the anastomotic connector 10D is deployed within an artery.

As discussed above with regard to the mesh frames of anastomotic connectors 10A-10C, mesh frames 44 and 47 of bonnet 40 and side access port 41, respectively, may be either self-expanding or non self-expanding, and may be formed using any suitable material. For example, both bonnet 40 and side access port 41 of anastomotic connector 10D may be structured as an ePTFE covered self-expanding mesh frame formed from nitinol, or a non self-expanding mesh frame formed from stainless steel or titanium. However, as discussed above with reference to anastomotic connector 10A, any suitable mesh frame material and cover material may be used without departing from the intended scope of the present invention.

Figure 7:
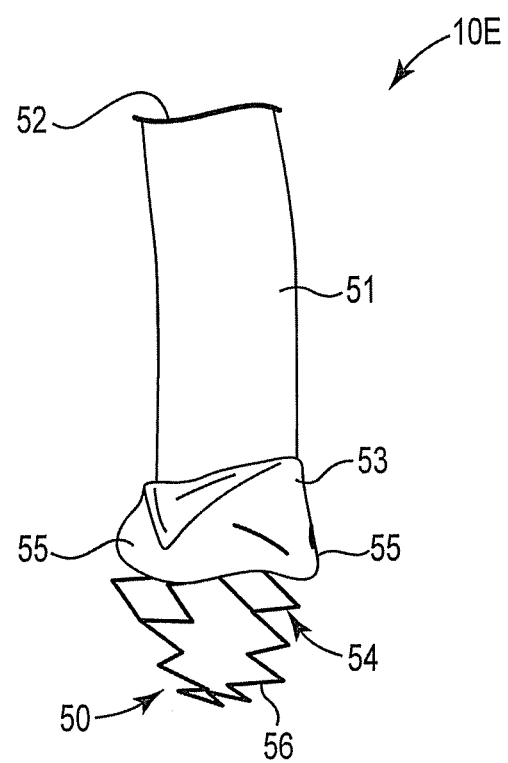
FIG. 7 is a perspective view of a fifth exemplary embodiment of an anastomotic connector in accordance with the present invention.

FIG. 7 is a perspective view of another exemplary anastomotic connector 10E in accordance with the present invention. Anastomotic connector 10E is similar to anastomotic connector 10C previously described above with reference to FIGS. 3, 4, and 5A-5C, and generally includes a main body or bonnet 50 with a side access port 51 extending outwardly therefrom. Once again, side access port 51 extends substantially perpendicular from bonnet 50 and includes an open first end 52 and a second end 53 that is in fluid communication with an interior of bonnet 50. Bonnet 50, which is partially reinforced by a mesh frame 54, includes an upper portion adjacent to second end 53 of side access port 51 having a pair of flanges 55 and a lower portion having a retention strap 56 extending across the second end 53 of the side access port. However, unlike anastomotic connector 10C, the flanges 55 are not reinforced by the mesh frame 54 and the biocompatible covering has been removed from the retention strap 56 thereby exposing the "bare" mesh frame 54.

As discussed above with regard to the mesh frames of anastomotic connectors 10A-10D, mesh frame 54 be either self-expanding or non self-expanding, and may be formed using any suitable material. Furthermore, the upper portion of the bonnet 50 and the side access port 51 may be formed from any suitable biocompatible material as will be appreciated by those skilled in the art.

The various anastomotic connector embodiments described above with reference to FIGS. 1-7 were presented merely for purposes of example and not limitation. Numerous other variations are also possible as will be appreciated by those skilled in the art based upon the present disclosure.

One exemplary use of the anastomotic connectors of the present invention is to provide means for attaching a tubular member between an artery and a vein in order to provide a fluid path therebetween. Examples of such tubular members may include, but are not limited to, a dialysis graft. As will be appreciated by those skilled in the art, the tubular member may be coupled to the side access port so as to provide a path for fluid away from the implanted connector device. In one exemplary embodiment the tubular member may be formed integral with the side access port. Alternatively, the tubular member may be formed as a separate component that may be slid over or otherwise attached to the side access port to form a leak free seal. When formed as a separate component, the tubular member may be attached to the side access port with any suitable attachment means including, but not limited to, heat welding or an adhesive. Additionally, a sealing gasket may also be used. The tubular member may be formed from any suitable biocompatible material, such as ePTFE.

The "flexible" and "expandable" nature of the anastomotic connectors of the present invention allows the connectors to be compressed and implanted through the sidewall of an artery or similar fluid passageway. With particular regard to the anastomotic connectors 10C-10E having the "bonnet" design, when inserted into the interior of an artery the retention strap may be expanded (either self-expansion or mechanical-expansion) against the far side wall of the artery that is opposite the access opening formed through the sidewall. Because the diameter of the bonnet is sized similar to or slightly larger than the internal diameter of the artery into which the connector is deployed, expansion of the bonnet exerts a radial force upon the internal arterial wall adjacent to the location of the side access port. This radial force acts to hold the anastomotic connector in the desired position and prevent the connector from becoming dislodged and potentially disrupting flow within the artery. The main body 12 of anastomotic connector 10A functions in a similar manner to the bonnets, but provides a radial force against a larger internal arterial surface area.

More particularly, in one exemplary method of positioning or deploying the anastomotic connectors of the present invention, the connectors may be deployed with a catheter type mechanism. For example, a needle access aperture may first be made into the target artery through the intended implant site of the connector. A guidewire may then be guided through the inserted needle. Once the guidewire is fully inserted, the needle may be retracted while leaving the guidewire in position. Next, a deployment catheter that is "pre-loaded" with a compressed anastomotic connector may be slid over the guidewire. Particularly, the pre-loaded anastomotic connector may be pushed through the deployment catheter and through the arterial wall into the desired position within the artery. Once the anastomotic connector is positioned within the artery, the particular "anchoring mechanism" associated with the connector may be deployed. Various examples of such anchoring structures include, but are not limited to, the main body of anastomotic connector 10A, the flanged distal end of anastomotic connector 10B, and the bonnets of anastomotic connectors 10C-10E. As will be appreciated by those skilled in the art, when non self-expanding anastomotic connectors are utilized, the deployment catheter may include an expansion means.

Figure 8A:
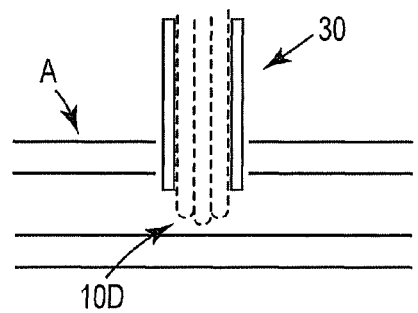
FIGS. 8A-8C are diagrams illustrating one exemplary method of deploying an anastomotic connector in accordance with the present invention.
Figure 8B:
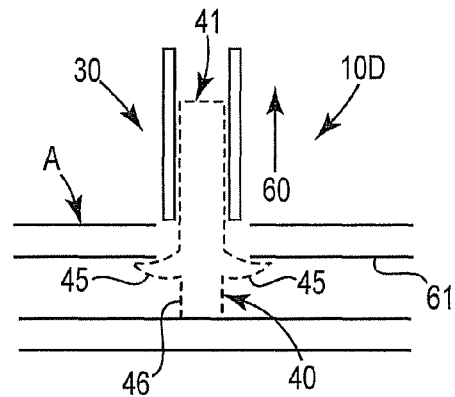
Figure 8C:
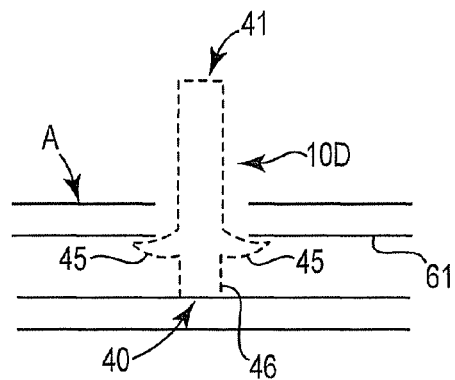

Further details regarding an exemplary method of deploying an anastomotic connector in accordance with the present invention are illustrated in FIGS. 8A-8C. Particularly, FIGS. 8A-8C illustrate the deployment of anastomotic connector 10D having both a self-expanding access port and bonnet. However, the exemplary deployment method is described with reference to anastomotic connector 10D merely for purposes of example and not limitation. Thus, workers skilled in the art will appreciate that the various other embodiments of the present invention may be deployed in a similar manner. As shown in FIG. 8A, a deployment sheath 30 with the anastomotic connector compressed and pre-loaded therein is introduced into a target artery A (post needle and guidewire insertion). Then, as shown in FIG. 8B, the deployment sheath 30 is pulled proximally in the direction indicated by arrow 60 to allow the bonnet 40 with the retention strap 46 to expand within the artery. While the connector is being deployed, the physician may verify that the connector placement is accurate by feeling the resistance of the bonnet flanges 45 against the internal arterial wall 61. Next, as shown in FIG. 8C, the deployment sheath 30 is fully removed and side access port 41 exerts radial force against the opening formed in the artery. Because the diameter of the side access port 41 is sized similar to or slightly larger than the diameter of the opening in the artery, the radial force exerted by the side access port 41 is resisted by the arterial wall, thereby creating a "compression fit" therebetween. The retention strap 46 of the bonnet 40 is structured to exert radial force on the arterial wall to provide stability and prevent collapsing of the artery near the anastomotic connector. As will be appreciated by those skilled in the art, the radial forces exerted by the side access port 41 and bonnet 40 function to securely maintain the anastomotic connector in the desired implantation position. In addition to functioning as a "stop" to let the physician know where the connector is during deployment, the bonnet flanges 45 may also provide additional stability to the connector device. The width of the retention strap may be less than that of the flanges to facilitate insertion into the vessel. As will be appreciated by those skilled in the art, the pair of flanges and the retention strap allow the passage of fluid (blood, etc.) to the distal tissues that the native vessel is supplying.

Figure 9A:
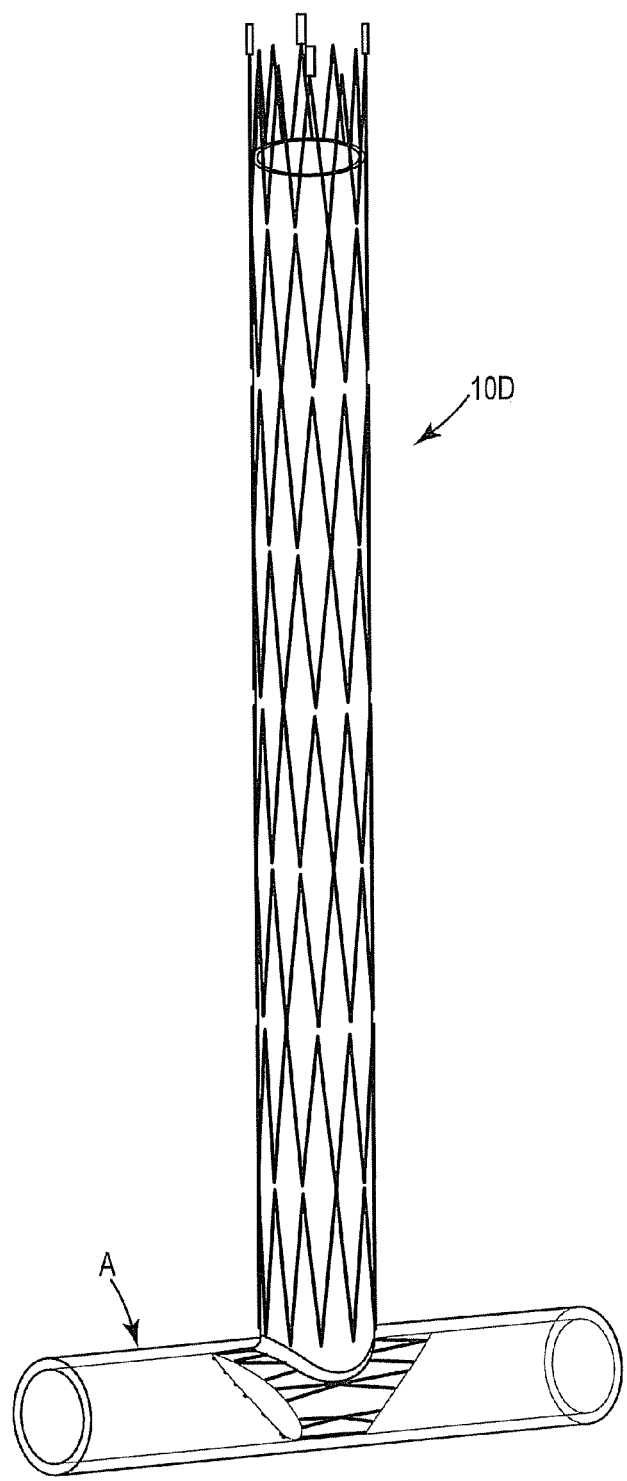
FIGS. 9A-9C are diagrams illustrating various embodiments of an anastomotic connector in accordance with the present invention deployed within an artery.
Figure 9B:
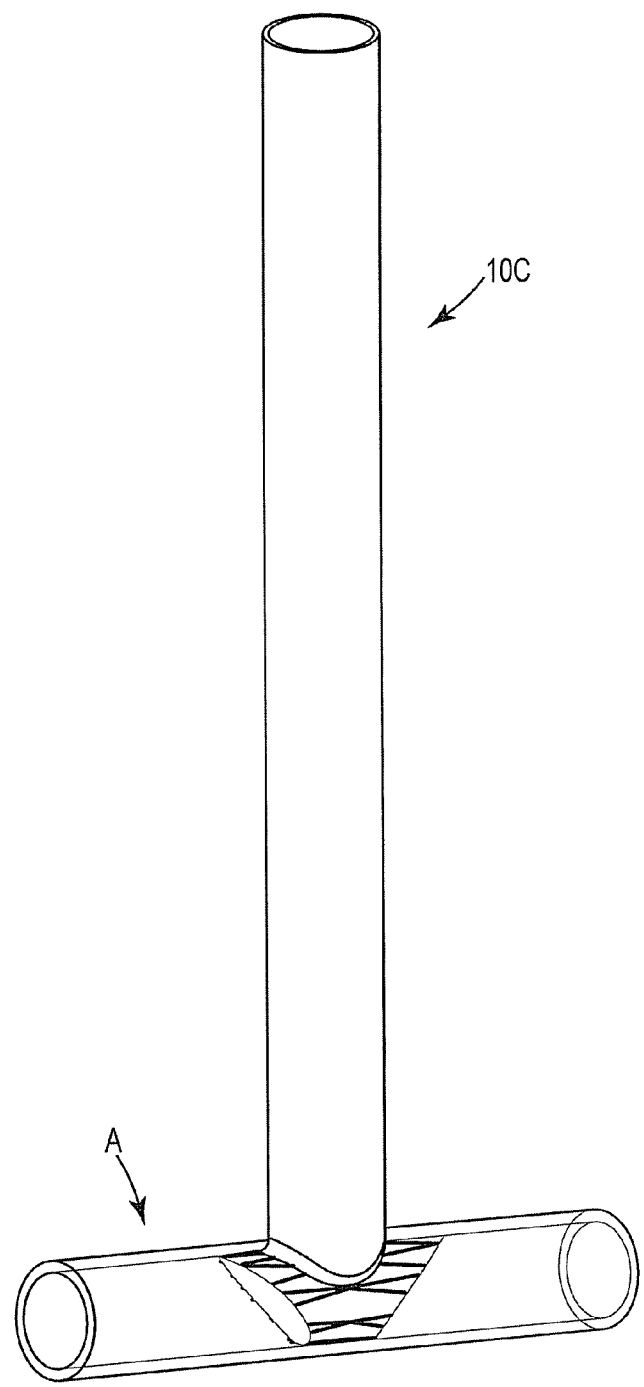
Figure 9C:
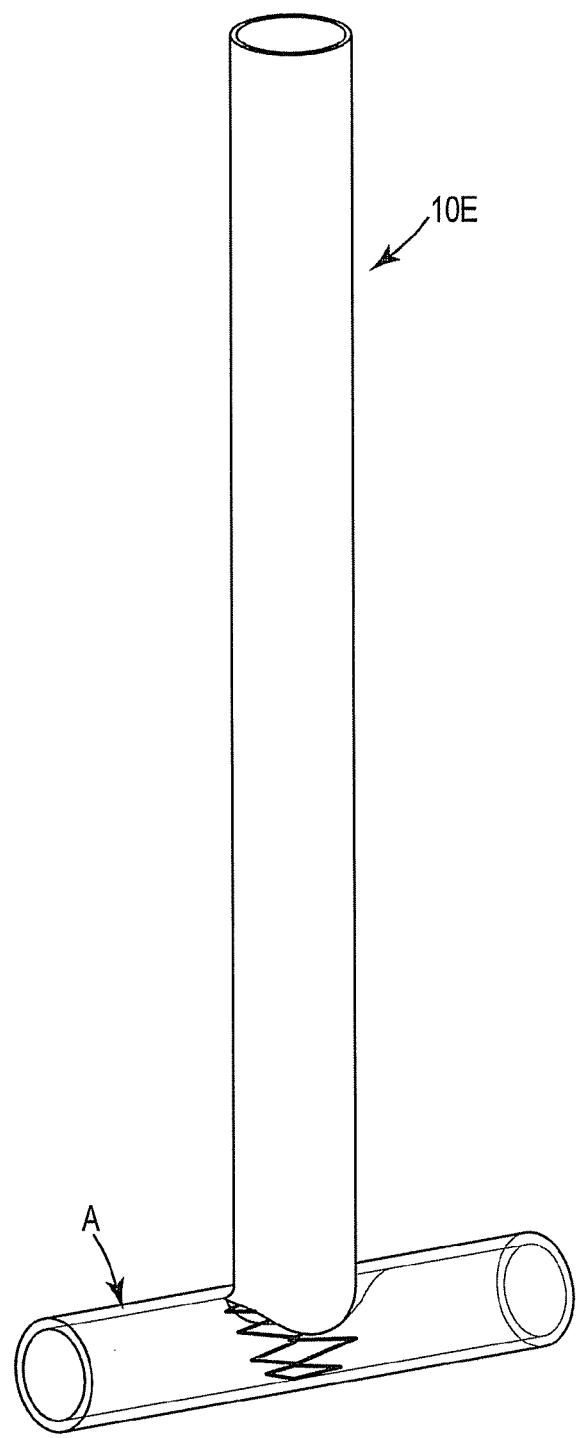

FIG. 9A is an exemplary diagram illustrating anastomotic connector 10D deployed within an artery A after utilizing the deployment method of FIGS. 8A-8C. Similarly, FIGS. 9B and 9C are exemplary diagrams illustrating anastomotic connectors 10C and 10E, respectively, deployed within an artery A using the disclosed deployment method.

As will be appreciated by those skilled in the art, the same general process illustrated in FIGS. 8A-8C may be followed in order to place a connector within other types of fluid passageways, such as within a vein.

Although FIGS. 8A-8C generally illustrate a method of deploying a self-expanding anastomotic connector, the method may be adapted for deploying an anastomotic connector having at least one portion that is non self-expanding. For example, consider first an embodiment wherein the retention strap is formed from a self-expanding material and the side access port is formed from a non self-expanding material. The deployment procedure may begin by using a needle or other suitable puncturing or cutting means to create an access aperture in a target artery at the intended implant site of the connector. A guidewire may then be guided through the inserted needle. Once the guidewire is fully inserted, the needle may be retracted while leaving the guidewire in position. Next, a deployment sheath having the anastomotic connector pre-loaded therein may be introduced into the target artery. Then, the deployment sheath may be pulled back in a proximal direction to expose the flanged portion of the bonnet and the retention strap within the artery (or alternatively, the anastomotic connector may be pushed out of the sheath). Because the retention strap is formed from a self-expanding material, the retention strap will expand once it is no longer contained by the deployment sheath. Subsequently, the non self-expanding side access port of the anastomotic connector may be "mechanically" expanded with any suitable expansion means as will be appreciated by those skilled in the art.

Consider next an embodiment wherein both the side access port and the retention strap are formed from non self-expanding materials. During deployment of the anastomotic connector, the side access port may be expanded by an expansion means such that the side access port exerts radial force against the opening formed in the artery as discussed above. In one exemplary embodiment, the side access port may be expanded to a predefined diameter prior to the dialysis graft being coupled to or positioned over the outer diameter of the side access port. Alternatively, in another exemplary embodiment, the side access port may be expanded against the dialysis graft after the graft has been coupled to or positioned over the non-expanded side access port. Next, the retention strap may be expanded against the internal arterial wall with an expansion means that is inserted through the expanded side access port. Once expanded, the retention strap may be structured to exert radial force on the arterial wall to provide stability and prevent collapsing of the artery near the anastomotic connector.

As will be appreciated by those skilled in the art, any suitable expansion means that is insertable through the delivery sheath may be used in accordance with the present invention. In one exemplary embodiment, the expansion means may be a balloon expanding support structure. Furthermore, the balloon expanding support structure may be expanded by filling the interior portion of the support structure with, for example, air or a saline solution. Other suitable expansion means include, but are not limited to, dilators or additional stents.

Based upon the present disclosure and after viewing the various embodiments of the anastomotic connectors presented herein, the many advantages and benefits provided by the present invention will be appreciated by those skilled in the art. One advantage is that the geometry of the anastomotic connectors allows continuous and uninterrupted arterial or venous flow during use for dialysis or other applications, thereby eliminating or substantially reducing any loss of circulation to the downstream, distal extremities. Stated alternatively, the geometry of the anastomotic connectors allows "full" flow into the graft or fistula as well as "full" flow to the downstream anatomy. Thus, distal arterial flow is not "cut-off" due to the presence of the anastomotic connector. Another advantage is that the anastomotic connectors of the present invention may be implanted percutaneously rather than with an "open surgery" approach. The implantation method is therefore less invasive for the patient and faster for the surgeon. Yet another advantage is that the present invention allows for maturation of the distal vein in preparation for secondary AVF while avoiding a central dialysis catheter.

Although the present invention has been described with reference to preferred embodiments, workers skilled in the art will recognize that changes may be made in form and detail without departing from the spirit and scope of the invention.

What is claimed is:

1. An anastomotic connector comprising: a generally tubular access port having a first end and a second end; and a main body portion in fluid communication with the second end of the access port and structured to be deployed within a fluid passageway, the main body portion including a self-expanding mesh frame defining a pair of self-expanding flanges extending radially outwardly from the second end of the access port to form a lateral axis, said pair of self-expanding flanges structured to alone exert a radial force solely against a first portion of an internal surface of the fluid passageway; and a self-expanding retention strap formed with said self-expanding flanges, said self-expanding retention strap having a longitudinal axis that is substantially perpendicular to the lateral axis of said flanges, said retention strap and said flanges having a substantially T-shaped structure in cross-section, as viewed along an axis substantially perpendicular to said longitudinal axis and said lateral axis, said retention strap extending across the second end of the access port and structured to exert a radial force solely on a second portion of the internal surface of the fluid passageway, said second portion of the internal surface opposing said first portion of the internal surface of the fluid passageway against which said pair of self-expanding flanges are structured to alone exert said radial force.

2. The anastomotic connector of claim 1, wherein said main body portion include a side access port extending substantially perpendicular from the main body portion.

3. The anastomotic connector of claim 1, wherein the mesh frame is formed from Nitinol.

4. The anastomotic connector of claim 1, wherein the mesh frame of the main body portion includes a biocompatible covering.

5. The anastomotic connector of claim 4, wherein the biocompatible covering is formed on an inner side of the mesh frame.

6. The anastomotic connector of claim 4, wherein the biocompatible covering is formed on an outer side of the mesh frame.

7. The anastomotic connector of claim 4, wherein the biocompatible covering comprises expanded Polytetrafluoroethylene (ePTFE).

8. The anastomotic connector of claim 1, wherein the generally tubular access port includes self-expanding mesh frame.

9. The anastomotic connector of claim 4, wherein the mesh frame of the access port includes an expanded Polytetrafluoroethylene (ePTFE) covering.

* * * * *